July 30, 1968 V. GATTI Plant Pat. 2,824

AZALEA PLANT

Filed Nov. 22, 1966

INVENTOR: VICTOR GATTI

United States Patent Office

Plant Pat. 2,824
Patented July 30, 1968

2,824

AZALEA PLANT

Victor Gatti, 150 Britton St., San Francisco, Calif. 94134

Filed Nov. 22, 1966, Ser. No. 597,832
1 Claim. (Cl. Plt.—56)

This invention is a new and distinct variety of azalea plant characterized in particular by its long lasting, salmon pink, double flowers, its ease of reproduction from cuttings, its rapid, many branched habit of growth and its high value as a greenhouse forcing variety.

The instant variety is a sport of the variety Emellia Gatti (Pat. No. 1,866, owned by me), and developed at my nursery, the location of which is 150 Britton Street, San Francisco, State of California.

I recognized in the sport as it developed that the color of the flowers was almost identical with the color of the flowers of the variety Paul Schame (not patented), but there were more petals in the flowers and the lasting quality was much better. Unlike Paul Schame, the flowers do not shatter or fall prematurely. Consequently, the plants seemed to have a greater market value.

Experimental asexual reproduction from cuttings taken from the original sport carried forward all the novel characteristics of the parent. The experimental propagation took place at my nursery at 150 Britton Street, San Francisco, Calif. Subsequent propagation has proven all the novel characteristics to be stable.

Figure 1:
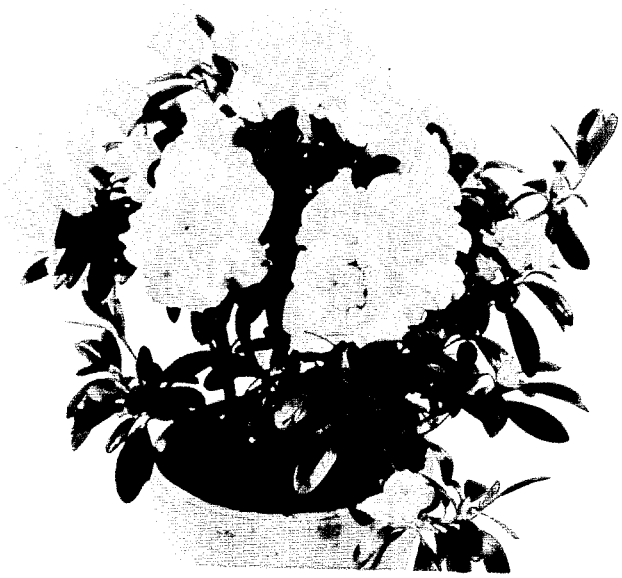
FIGURE 1 is a perspective view showing a plant of the instant variety at near full open flower stage and at about one third (⅓) natural size.
Figure 2:
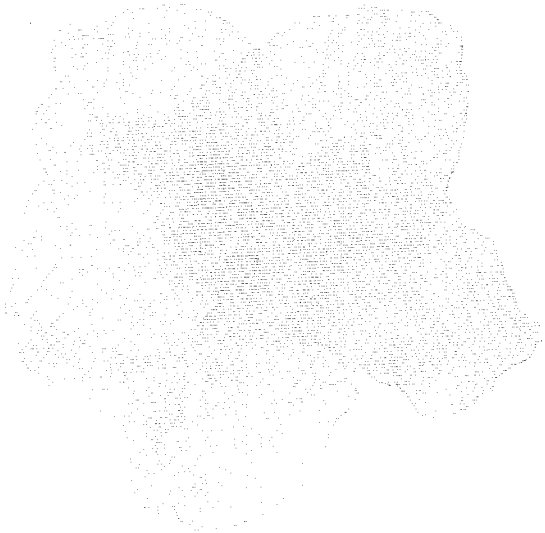
FIGURE 2 is a perspective view showing the petal formation which runs quite uniform from flower to flower.

Referring now more specifically to the botanical details of the new and distinct variety of azalea plant, the following is an outline description of the same:

Plant:

*Form.*—Well branched, symmetrical. It develops into a plant of greater breadth than height.

*Growing habit.*—Dense and bushy with an abundance of medium green leaves of good texture and quality. It develops quickly into a well-shaped, spreading plant with a minimum of pinching.

*Blooming habit.*—Profuse, flowering evenly over the entire plant at nearly the same time when forced in the greenhouse or flowered naturally under lath.

*Blooming season.*—Plants growing under lath under San Francisco conditions bloom naturally in early to mid-March. As a greenhouse forcer it is medium early.

Foliage:

*Size.*—Maximum size of mature leaves on blooming size plants about two inches to two and one-quarter inches long (2 to 2¼ inches) and five-eighths to seven-eighths inch (⅝ ⅞ inch) wide, each plant having many smaller leaves.

*Color.*—On mature plants growing under optimum conditions, the leaves are a medium green (approximately Plate 24–J–8), lighter beneath.

*Shape.*—Elliptical.

*Aspect.*—Smooth and glossy, with some minute hairs.

*Texture.*—Medium.

*Edge.*—Without serrations, some minute hairs.

*Ribs and veins.*—Normal.

Flower:

*Size.*—Two and one-half (2½) inches to three (3) inches across.

*Borne.*—One or two flowers from each bud, two or more buds often set on a single branch.

*Petiole.*—About one-half (½) inch long, it is strong and holds the flower up well.

*Form.*—Commonly called double, the stamens having become petals and petaloids.

*Permanence.*—Long lasting, retaining the attractive color until the flowers wither. Does not shatter or drop prematurely; withered flowers must be removed.

*Color.*—Salmon pink (Plate 2–J–8), lighter or darker as color is influenced by cultural or light conditions.

Petals:

*Texture.*—Substantial.

*Arrangement.*—Normal for the type.

*Persistence.*—Remains firm for the life of the flower.

Reproductive organs:

*Stamens.*—Norman stamen development has never been observed in the instant variety.

*Pistil.*—Norman pistil development is rare and is not uniform, varying greatly from flower to flower and often consists of several sections joined together at the base. Style color is similar to the color of the petals. Stigma brownish.

*Ovule.*—Poor, incomplete development in most of the flowers. Good development occurs with normal pistil development.

Comparison: The instant variety has some resemblance in flower color and plant habit to the popular azalea variety Paul Schame (not patented), the principal difference being more petals for greater beauty and the longer lasting quality of the flowers to enhance the market value. The faster growing and better branching habit of the plant aids in producing a greater number of branches and consequently more flowers and a better market value.

All color plate identifications refer to "A Dictionary of Color" by Maerz and Paul.

Having thus described the invention, I claim:

A new variety of azalea plant which is a distinctive improvement over azalea varieties producing flowers of a similar color in the following particulars:

(a) The flowers have more petals and last much longer.

(b) The plant has a better branching habit; consequently it is easier to produce plants having a top market value.

No reference cited.

ROBERT E. BAGWILL, *Primary Examiner.*